(12) United States Patent
Salah et al.

(10) Patent No.: US 10,799,321 B2
(45) Date of Patent: Oct. 13, 2020

(54) METHOD FOR MONITORING THE POSITION OF TEETH

(71) Applicant: DENTAL MONITORING, Paris (FR)

(72) Inventors: Philippe Salah, Paris (FR); Emmanuel Salah, Aulnay sous Bois (FR); William Ayache, Neuilly sur Seine (FR)

(73) Assignee: DENTAL MONITORING, Paris (FR)

( * ) Notice: Subject to any disclaimer, the term of this patent is extended or adjusted under 35 U.S.C. 154(b) by 0 days.

(21) Appl. No.: 15/023,537

(22) PCT Filed: Sep. 19, 2014

(86) PCT No.: PCT/IB2014/064658
§ 371 (c)(1),
(2) Date: Mar. 21, 2016

(87) PCT Pub. No.: WO2015/040577
PCT Pub. Date: Mar. 26, 2015

(65) Prior Publication Data
US 2016/0228212 A1    Aug. 11, 2016

(30) Foreign Application Priority Data

Sep. 19, 2013    (FR) ...................... 13 59038

(51) Int. Cl.
*A61C 7/00*        (2006.01)
*G16H 50/50*    (2018.01)
(Continued)

(52) U.S. Cl.
CPC ............ *A61C 7/002* (2013.01); *A61B 5/0013* (2013.01); *A61B 5/1111* (2013.01); *A61B 5/681* (2013.01);
(Continued)

(58) Field of Classification Search
CPC ..... A61C 7/002; A61C 9/0053; A61B 5/0013; A61B 5/1111; A61B 5/681; A61B 5/6897;
(Continued)

(56) References Cited

U.S. PATENT DOCUMENTS 5,278,756 A * 1/1994 Lemchen ............... A61C 19/04
128/920
6,328,567 B1  12/2001 Morris et al.
(Continued)

FOREIGN PATENT DOCUMENTS

CA        2292141 A1    6/2001
CN     201244032 Y      5/2009
(Continued)

OTHER PUBLICATIONS

Braces Guide: Retainer Check Appointments (2015).*
(Continued)

*Primary Examiner* — Yogesh P Patel
(74) *Attorney, Agent, or Firm* — Oliff PLC

(57) ABSTRACT

A method for monitoring the position of the teeth of a patient includes the following steps: a) modeling a target position of the teeth in the form of a target model; b) after a time interval, modeling an updated position of the teeth in the form of an updated model; c) comparing the target and updated models.

15 Claims, 1 Drawing Sheet

(51) Int. Cl.
*A61B 5/00* (2006.01)
*A61B 5/11* (2006.01)
*A61C 9/00* (2006.01)

(52) U.S. Cl.
CPC .......... *A61B 5/6897* (2013.01); *A61B 5/6898* (2013.01); *A61C 9/0053* (2013.01); *G16H 50/50* (2018.01); *A61B 2576/02* (2013.01)

(58) Field of Classification Search
CPC .............. A61B 5/6898; A61B 2576/02; G06F 19/3437; G06Q 10/1095; G06Q 50/22
USPC .............. 433/24; 700/98; 382/154; 250/234; 356/601
See application file for complete search history.

(56) References Cited

U.S. PATENT DOCUMENTS

| | | | |
|---|---|---|---|
| 6,431,870 | B1 | 8/2002 | Sachdeva |
| 6,793,489 | B2 | 9/2004 | Morris et al. |
| 8,562,338 | B2 | 10/2013 | Kitching et al. |
| 8,684,729 | B2 | 4/2014 | Wen |
| 8,738,165 | B2* | 5/2014 | Cinader, Jr. ............. A61C 7/00 700/98 |
| 8,998,609 | B2 | 4/2015 | Prakash et al. |
| 9,039,412 | B2 | 5/2015 | Rose et al. |
| 9,572,637 | B2 | 2/2017 | Jinkyun |
| 9,861,451 | B1 | 1/2018 | Davis |
| 2002/0015934 | A1 | 2/2002 | Rubbert et al. |
| 2003/0224314 | A1* | 12/2003 | Bergersen ................ A61C 7/08 433/6 |
| 2004/0038168 | A1* | 2/2004 | Choi ........................ A61C 7/00 433/24 |
| 2004/0197727 | A1 | 10/2004 | Sachdeva et al. |
| 2004/0252303 | A1 | 12/2004 | Giorgianni et al. |
| 2005/0048432 | A1 | 3/2005 | Choi et al. |
| 2005/0123180 | A1 | 6/2005 | Luo et al. |
| 2006/0127854 | A1 | 6/2006 | Wen |
| 2006/0136267 | A1* | 6/2006 | Brackett .............. A61B 5/0002 705/3 |
| 2006/0177789 | A1 | 8/2006 | O'Bryan |
| 2006/0199140 | A1 | 9/2006 | Wen |
| 2006/0199142 | A1 | 9/2006 | Liu et al. |
| 2008/0206700 | A1* | 8/2008 | Korytov ................... A61C 7/00 433/2 |
| 2008/0306724 | A1 | 12/2008 | Kitching et al. |
| 2008/0318179 | A1 | 12/2008 | Liu |
| 2009/0079993 | A1 | 3/2009 | Yatagai et al. |
| 2009/0291417 | A1 | 11/2009 | Rubbert et al. |
| 2010/0042440 | A1 | 2/2010 | Joao |
| 2011/0268327 | A1 | 11/2011 | Getto et al. |
| 2013/0017506 | A1* | 1/2013 | Parker ..................... A61C 7/28 433/24 |
| 2013/0044932 | A1* | 2/2013 | Caligor ................... A61B 6/14 382/132 |
| 2013/0059262 | A1* | 3/2013 | Farrell ..................... A61C 7/08 433/6 |
| 2013/0127825 | A1* | 5/2013 | Joshi ....................... G06T 19/20 345/419 |
| 2013/0215383 | A1 | 8/2013 | Siminou |
| 2013/0216971 | A1 | 8/2013 | Friddell |
| 2013/0286174 | A1* | 10/2013 | Urakabe ............ A61B 1/00009 348/66 |
| 2013/0345524 | A1* | 12/2013 | Meyer ................... G06F 19/363 600/301 |
| 2014/0147807 | A1 | 5/2014 | Yau et al. |
| 2014/0204118 | A1 | 7/2014 | Berry et al. |
| 2014/0221819 | A1 | 8/2014 | Sarment |
| 2014/0379356 | A1* | 12/2014 | Sachdeva ............... A61C 7/002 705/2 |
| 2015/0127266 | A1 | 5/2015 | Chen |
| 2015/0157209 | A1* | 6/2015 | Dantus ................ A61B 5/0075 600/317 |
| 2015/0320320 | A1 | 11/2015 | Kopelman et al. |
| 2016/0004811 | A1 | 1/2016 | Somasundaram et al. |
| 2016/0012182 | A1 | 1/2016 | Golay |
| 2016/0220105 | A1 | 8/2016 | Duret |
| 2016/0228212 | A1 | 8/2016 | Salah et al. |
| 2017/0215998 | A1 | 8/2017 | Kopelman et al. |
| 2017/0236298 | A1 | 8/2017 | Vetter |
| 2018/0055600 | A1 | 3/2018 | Matov et al. |
| 2018/0125610 | A1 | 5/2018 | Carrier, Jr. et al. |

FOREIGN PATENT DOCUMENTS

| | | |
|---|---|---|
| EP | 3050534 A1 | 8/2016 |
| FR | 1460310 A | 11/1966 |
| FR | 3010629 A1 | 3/2015 |
| JP | 5241971 B1 | 7/2013 |
| KR | 10-2018-0008532 A | 1/2018 |
| WO | 2001/051005 A2 | 7/2001 |
| WO | 2006/065955 A2 | 6/2006 |
| WO | 2013/090843 A1 | 6/2013 |
| WO | 2015-082300 A1 | 6/2015 |
| WO | 2017/182648 A1 | 10/2017 |
| WO | 2017/182654 A1 | 10/2017 |

OTHER PUBLICATIONS

Krieger, Glenn. "It's not about the dental camera . . . ". Blog. Dental Photography Pearls for Better Images Instantly. Blogspot, Mar. 14, 2012 Published. Web. Nov. 9, 2017 Accessed. <http://dentalphotography.blogspot.com/2012/03/its-not-about-camera_14.html#.WgTKKzN95OR>.*
Dec. 8, 2014 Search Report issued in International Patent Application No. PCT/IB2014/064658.
Dec. 8, 2014 Written Opinion issued in International Patent Application No. PCT/IB2014/064658.
Fleischmann, Georg, "Cenon: The CAM User's Guide, Version 4.0", http://www.Cenon.com, pp. 1-174 (2014).
Toet, Alexander, "Target Detection and Recognition through Contour Matching", CALMA Report CALMA.TNO.WP31.AT.95b, pp. 1-32 (1994).
"Smile Capture", Style Italiano, www.styleitaliano.org/smile-capture/, pp. 1-20, 2014 (retrieved Aug. 8, 2015).
Ahmad, Irfan, "Digital dental photography Part 8: intra-oral set-ups", British Dental Journal, vol. 207, pp. 151-157 (2009).
Jan. 7, 2016 Written Opinion issued in International Patent Application No. PCT/EP2015/074895.
U.S. Appl. No. 15/522,523, filed Apr. 27, 2017 in the name of Salah et al.
Jan. 12, 2016 Written Opinion issued in International Patent Application No. PCT/EP2015/074896.
U.S. Appl. No. 15/522,520, filed Apr. 27, 2017 in the name of Salah et al.
Feb. 24, 2016 Written Opinion issued in International Patent Application No. PCT/EP2015/074868.
U.S. Appl. No. 15/522,576, filed Apr. 27, 2017 in the name of Salah et al.
Jan. 26, 2016 Written Opinion issued in International Patent Application No. PCT/EP2015/074897.
U.S. Appl. No. 15/522,554, filed Apr. 27, 2017 in the name of Salah et al.
Jan. 13, 2016 Written Opinion issued in International Patent Application No. PCT/EP2015/074900.
U.S. Appl. No. 15/522,430, filed Apr. 27, 2017 in the name of Salah et al.
Feb. 18, 2016 Written Opinion issued in International Patent Application No. PCT/EP2015/074859.
U.S. Appl. No. 15/522,606, filed Apr. 27, 2017 in the name of Salah et al.
Jul. 3, 2018 Office Action issued in U.S. Appl. No. 15/522,576.
May 30, 2018 Office Action issued in U.S. Appl. No. 15/522,606.
Rails, et al., "Computer-Assisted Dental Diagnosis," Dental Clinics of North America, vol. 30, No. 4, Oct. 1986, pp. 695-712.

(56) References Cited

OTHER PUBLICATIONS

U.S. Appl. No. 16/094,245, filed Oct. 17, 2018 in the name of Salah et al.
U.S. Appl. No. 16/094,255, filed Nov. 9, 2018 in the name of Salah et al.
U.S. Appl. No. 15/990,950, filed May 29, 2018 in the name of Salah et al.
U.S. Appl. No. 16/001,049, filed Jun. 6, 2018 in the name of Salah et al.
U.S. Appl. No. 16/031,201, filed Jul. 10, 2018 in the name of Salah et al.
Taner, et al., "Evaluation of dental arch width and form changes after orthodonic treatment and tention with a new computerized method," American Journal of Orthodontics and Dentofacial Orthopedics, vol. 126, No. 4, Oct. 2004. pp. 464-475.
Aug. 1, 2019 Office Action Issued in U.S. Appl. No. 15/522,523.
Aug. 8, 2019 Office Action Issued in U.S. Appl. No. 15/522,554.
Nov. 29, 2018 Office Action issued in U.S. Appl. No. 15/522,554.
Oct. 4, 2019 Office Action issued in U.S. Appl. No. 15/952,635.
Dec. 2, 2019 Office Action issued in U.S. Appl. No. 16/240,525.
Mar. 19, 2020 Office Action issued in U.S. Appl. No. 15/522,554.
Jan. 2, 2019 Office Action issued in U.S. Appl. No. 15/522,520.
Jan. 4, 2019 Office Action issued in U.S. Appl. No. 15/522,576.
Jul. 27, 2020 Office Action issued in U.S. Appl. No. 15/522,523.

\* cited by examiner

METHOD FOR MONITORING THE POSITION OF TEETH

TECHNICAL FIELD

The present invention relates to a method for monitoring the position of a patient's teeth, and to a computer program for implementing this method.

PRIOR ART

After an orthodontic treatment, it is necessary for the treated patient to have his teeth monitored on a regular basis, especially in order to check that the position of the teeth has not developed unfavorably. This unfavorable development is also called a "relapse". Traditionally, the patient therefore visits his orthodontist at regular intervals in order to have these checks carried out. He can also visit his dentist, who is also able to detect any imperfection in the position of the teeth.

Many patients fail to attend these checkups, which would allow any relapse situations to be detected. The teeth are therefore able to readopt a position of malocclusion which, in order to be corrected, requires new orthodontic treatment, and the latter may be as extensive as the initial treatment.

In addition, the visits are inconvenient for the patient and place stress on the orthodontist.

An object of the present invention is to solve, at least in part, the aforementioned problems.

SUMMARY OF THE INVENTION

The invention makes available a method for monitoring the position of a patient's teeth, said method comprising the following steps:
   a) modeling a target position of said teeth in the form of a target model;
   b) after a time interval, modeling an updated position of said teeth in the form of an updated model;
   c) comparing said target and updated models.

A method according to the invention may also include one or more of the following optional features:

the target model is a three-dimensional model;
the target model is a model of the position of the patient's teeth after an orthodontic treatment;
the target model corresponds to an actual position of the teeth, that is to say it is not a theoretical model corresponding to a future position at the time when step a) is carried out;
the target model supplies information concerning the position of the teeth with an error of less than 5/10 mm, preferably less than 3/10 mm, preferably less than 1/10 mm;
the time interval is longer than 1 month and/or is determined by the patient or, preferably, by an orthodontist;
step b) is carried out at a distance from step a), that is to say at a different location from the one in which step a) is carried out, in particular more than 50 m, more than 100 m or more than 1 km from the location where step a) is carried out, in particular outside the orthodontic practice;
step b) is not carried out in a dental practice, an orthodontic practice or an orthodontic laboratory;
use is made of an individual apparatus chosen from the group comprising a cell phone, a "connected" photographic apparatus, a smart watch, a digital tablet, a portable 3D scanner, and a computer linked to an image acquisition system, such as a webcam or a digital photographic apparatus, in order to implement step b) and/or step c), preferably step b) and step c);
the updated model comprises a video or a photo of the patient's teeth, preferably a photo of the patient from the front, a photo taken from the patient's right and a photo taken from the patient's left;
the updated model comprises a video of the patient's teeth;
step b) is preferably carried out by the patient or a relation of the patient, but it may be carried out by a dentist;
at step b), one or more photos and/or videos of the patient's teeth are processed in order to create a three-dimensional updated model;
prior to step c), preferably prior to step b), the patient or a dental professional loads the target model onto said individual apparatus or makes it available for loading onto said individual apparatus; the patient preferably downloads the target model from the Internet;
information is generated at step c), the content of which information depends on the difference or "distance" between the target model and updated model, and this information is preferably transmitted to said patient and/or to a dental professional;
depending on the comparison at step c), the patient and/or a dental professional is informed of the probable need for a consultation with a dentist or an orthodontist;
step c) concerning comparison of the models is carried out either on a personal apparatus of the patient's, or with an app used by a dental professional, or with a dedicated third-party server.

The invention also relates to the use of a method according to the invention in order to
   detect a relapse, and/or
   determine a speed of change in the position of the teeth, and/or
   optimize the scheduling of visits to an orthodontist or a dentist, and/or
   evaluate the efficacy of an orthodontic treatment, and/or
   evaluate the change of position of teeth toward a theoretical model corresponding to a defined position of the teeth, in particular an improved position of the teeth.

The invention also relates to a computer program and in particular to a specialized app configured for implementation of step b) and/or step c), preferably of both steps b) and c), a computer medium on which such a computer program is stored, for example a memory or a CD-ROM, and a personal apparatus, in particular a cell phone or a tablet, on which such a program is loaded.

The personal apparatus may in particular comprise an acquisition module and/or a processing module and/or a comparison module and/or a communication module having one or more of the features described below, so as to be able to execute one or more of the operations of a method according to the invention.

The invention also relates to a system comprising
   a dental professional,
   a patient,
said professional being equipped with an apparatus that is able to implement step a) of a method according to the invention, preferably in order to create a three-dimensional model of the dentition of said patient,
said patient being equipped with a personal apparatus, preferably a cell phone, on which a specialized app is loaded that is able to carry out steps b) and c) of a method according to the invention.

The professional can in particular be equipped with a three-dimensional scanner.

The invention relates, finally, to a method for therapeutic or cosmetic treatment comprising the following steps:

A. modifying the position of a patient's teeth by means of an active retainer apparatus, for example an aligner of the Invisalign® type, or an apparatus comprising an arch and brackets;

B. at the end of step A, that is to say after the position of the teeth has been corrected and the patient is no longer wearing an active retainer apparatus, checking for a relapse by means of a method for monitoring the position of the teeth according to the invention.

Definitions

A "patient" is understood as any person on whom a method is carried out in order to monitor the teeth, whether or not this person is ill.

A "dental professional" is understood as a dentist, an orthodontist or an orthodontic laboratory.

A "dentist" is understood as a dentist or a dental assistant working under the responsibility of a dentist.

A "cell phone" is an apparatus of less than 500 g, equipped with a sensor allowing it to record images, capable of exchanging data with another apparatus more than 500 km from the cell phone, and capable of displaying said data, especially said images.

A "tablet" is a portable computer with a touch-sensitive screen.

A 3D scanner is an apparatus with which it is possible to obtain a three-dimensional representation of an object.

The terms "comprising a" or "having a" are understood as meaning "having at least one", unless otherwise indicated.

BRIEF DESCRIPTION OF THE FIGURES

Other features and advantages of the invention will become clearer on reading the following detailed description and on studying the attached drawing, in which.

DETAILED DESCRIPTION

A method according to the invention has the steps a) to c) mentioned above.

Without limiting the scope of the invention, the method described below is implemented in order to monitor a relapse after an orthodontic treatment.

Figure 1:
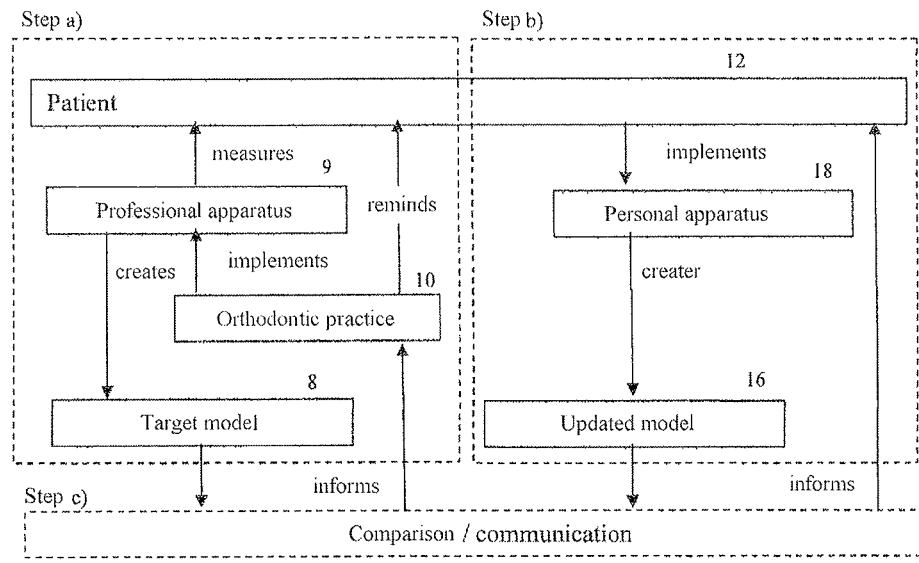
FIG. 1 and FIG. 2 illustrate, respectively, a method and the contents of a cell phone that may be used for carrying out a method according to the invention.

At step a), a target model 8 of the patient's teeth is created (see FIG. 1).

In the context of monitoring a relapse, the target model is a model of the teeth in their corrected position, resulting from the implementation of the orthodontic treatment. The target model is thus created after the orthodontic treatment, that is to say at a time when the patient is no longer wearing an active orthodontic retainer apparatus.

The target model may therefore also be called the "initial" model.

Preferably, the target model is prepared less than six months, preferably less than three months, more preferably less than one month, after the end of the orthodontic treatment, generally immediately after the end of the treatment. It thus corresponds to a substantially optimal position of the teeth.

The form of the target model is not limited. It can in particular be a three-dimensional digital model, but also an image, a two-dimensional photo, for example a panoramic photo, or a film. In one embodiment, the target model may be obtained by one or more measurements carried out on the teeth, for example the measurement of a space between two adjacent teeth.

Preferably, the target model is a three-dimensional digital model of the patient's dentition, for example of the type .stl or .Obj, .DXF 3D, IGES, STEP, VDA or point clouds. Advantageously, such "3D" models may be observed at any desired angle.

The target model may be prepared from measurements carried out on the patient's teeth or on a physical model of his teeth, for example a plaster model.

The target model is preferably created by means of a professional apparatus 9, preferably in an orthodontic practice, for example by means of a 3D scanner, preferably used by a healthcare professional, for example by an orthodontist or an orthodontic laboratory 10. In an orthodontic practice, the patient 12 or the physical model of his teeth may advantageously be placed in a precise position and the acquisition means may be sophisticated. This results in a very precise target model.

The target model may be stored in a centralized database that includes the target models from a plurality of patients. This database may be physically set up in a specialized establishment. It may also be set up in a laboratory or an orthodontic practice, which limits the transfer of confidential information.

In one embodiment, the target model, or a copy of the target model, is given to the patient. Preferably, a computer file corresponding to the target model is stored on a portable medium, for example on a USB stick or on an electronic card, preferably on a cell phone, a tablet or a portable computer of the patient's, in particular on the personal apparatus that will be used at step b).

At step b), after a time interval $\Delta t$, an updated model 16 is created.

The time interval $\Delta t$ may be predetermined. It may be constant, irrespective of the occurrence of the method, that is to say irrespective of whether this interval concerns the first execution of the method or a subsequent execution. It may be variable and depend, for example, on the results of an earlier step c). In particular, the time interval $\Delta t$ may be shorter when this earlier step c) has detected a considerable deviation.

In a preferred embodiment, the time interval $\Delta t$ is determined by the orthodontist according to a monitoring schedule. Depending on how the position of the teeth develops, the orthodontist is able to modify this schedule and thus modify the time interval $\Delta t$. In one embodiment, the monitoring method uses several cycles, each comprising a step b) and a step c), and the time intervals between each cycle may be identical or different. The time intervals between two successive cycles may all be determined before the first cycle is executed, in order to conform to a monitoring schedule planned by the orthodontist.

The time interval $\Delta t$ may also be indeterminate and depend, for example, on decisions of the patient. For example, an updated model may be created during a visit to the dentist or whenever the patient wishes this to be done.

The time interval $\Delta t$ is preferably determined to correspond to a potentially significant development in the position of the teeth. Preferably, for the first year after the treatment, the time interval $\Delta t$ is less than three months. After this first year, the time interval $\Delta t$ is preferably longer than one month, or even longer than six months or longer than twelve months. A time interval of between six months and eighteen months is suitable in particular for detecting a deviation of the teeth.

Preferably, the patient is sent at least one reminder informing the patient of the need for an updated model to be created. This reminder may be in paper form or, preferably, in electronic form, for example in the form of an e-mail, an automatic alert from the portable specialized app, or an SMS. A reminder of this kind may be sent by the orthodontic practice or laboratory 10, or by the dentist, for example.

The updated model may or may not be prepared like the target model. Its format may be identical to or different than that of the target model.

Preferably, the updated model 16 is created with a personal apparatus 18 currently available on the market, for example a cell phone or a tablet or a personal computer, either fixed or portable, preferably a photographic apparatus. The updated model 16 may in particular be created by the patient himself or by one of his relations. For this purpose, a specialized app is preferably loaded on the personal apparatus 18. The personal apparatus preferably weighs less than 3 kg, less than 2 kg, less than 1 kg, less than 500 g, preferably less than 300 g.

It is also preferable that the updated model 16 is produced from or is in the form of a photo, in particular a panoramic photo, or a film. In a preferred embodiment, the updated model is in the form of at least one photo, preferably at least three photos, corresponding to a view of the patient's teeth from the front, a view of the patient's teeth from the right and a view of the patient's teeth from the left. Photos may be taken either for the upper dental arch or for the lower dental arch or for both.

The personal apparatus preferably provides color images and/or infrared images of the patient's mouth or even of the patient's face. The infrared images advantageously show the teeth with excellent contrast.

Figure 2:
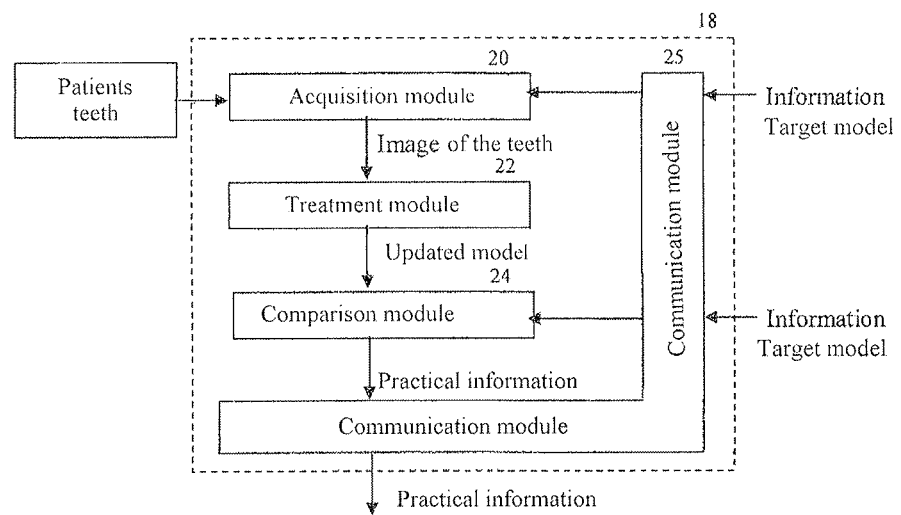

As is shown in FIG. 2, the personal apparatus 18 has an acquisition or "capture" module 20 and preferably a processing module 22, also preferably a comparison module 24, and preferably a communication module 25.

Preferably, the patient's personal apparatus has a specialized app having one or more of these modules, preferably all of these modules. It is also preferable that this app organizes the reminders and informs the patient of the need to create an updated model.

Preferably, the specialized app is loaded onto the personal apparatus from a physical support such as a USB stick or a CD-ROM or is downloaded from the Internet or by radio. In one embodiment, the specialized app is made available to the patient by the orthodontic practice and/or the orthodontic laboratory. It may in particular take the form of an app of the kind currently downloaded on iPhones with the Apple® trademark, or apparatuses of all brands using Android® operating systems or any other operating system.

The acquisition module 20 preferably has a photographic apparatus or a video or infrared camera which the user, for example the patient or one of his relations, positions by means of a viewfinder or a screen before activating it.

Preferably, the acquisition module 20 has error prevention means that make this positioning easier.

The user can be guided in the acquisition by written messages and/or voice messages. For example, the personal apparatus may announce "Take a photo from the front", emit a signal to inform the user that the photo is acceptable or, on the contrary, that he must take another photo, announce "Take a photo from the right", preferably by displaying an arrow in order to orient the user, etc. The end of the acquisition process may also be announced by the apparatus. The apparatus may also help in the positioning of the personal apparatus, for example by visual messages (for example by display of arrows) and/or audio messages (such as a succession of beeps whose frequency increases as the positioning of the apparatus improves) and/or written messages and/or voice messages ("higher", "lower", etc.).

The error prevention means may in particular have locating marks which appear on the viewfinder or the screen. The locating marks may, for example, include a line intended to be aligned with the general direction of the join between the upper teeth and the lower teeth when the teeth are closed by the patient, or a vertical line intended to be aligned with the join between the two upper incisors. The locating marks may also refer to other parts of the patient. For example, they may consist of marks corresponding to the position of the eyes or may take the form of a contour within which the patient's mouth or face has to be positioned. In one embodiment, the locating marks correspond to a reference system, for example in the form of a retractor or an intraoral imaging device, which is preferably given to the patient at a visit to his orthodontist or dentist, and which the patient has to position in a predetermined position during the acquisition. For example, the reference system may be intended to be bitten by the patient.

In a preferred embodiment, the error prevention means are defined, at least in part, on the basis of information supplied by the target model. For example, in accordance with the principles of "augmented reality", all or part of the target model, optionally reprocessed, may be rendered visible on said screen or said viewfinder during the acquisition.

The reprocessing of the target model in order to facilitate the acquisition, or "acquisition reprocessing", may comprise, for example, the creation of one or more images or a three-dimensional view in which the teeth appear in transparency. It may also involve the generation of two-dimensional images, in particular from a three-dimensional target model, for example the generation of a front view, a view from the right and a view from the left.

The acquisition reprocessing may be carried out, for example, on a dedicated server, preferably by a dental professional, in particular immediately after the creation of the target model. Advantageously, the dental professional may have computing power available by which it is possible to obtain sophisticated error prevention means. The acquisition reprocessing is preferably carried out by the personal apparatus, in particular with the specialized app.

Preferably, the information deriving from the target model and used to create the error prevention means is downloaded to the personal apparatus 18.

Preferably, at least part of the target model appears in transparency to the user during the acquisition. In one embodiment, only the contour of the teeth appears to the user. It is therefore very easy for the latter to superpose the target model which appears in transparency with the teeth of the patient that he must take a photo of or film. In particular, when the creation of the updated model requires one or more photos to be taken, preferably photos from the front, from the right and from the left, the screen or the viewfinder preferably displays a corresponding view of the target model, preferably a line-type representation.

If the acquisition is made by video or by panoramic imaging, a real-time pre-rendering may be effected during the acquisition. This pre-rendering will guide the user on the missing zones and/or will select the photos or video images that are clearest or best interpolated to construct the updated model.

Preferably, the processing module 22 is configured to transform the information acquired by the acquisition model, for example photos, to an updated model that can be compared with the target model. The processing module 22 may, for example, process the acquired images in order to create a digital updated model, preferably in three dimensions.

Preferably, the processing module 22 also has means for refining the acquired information. For example, by comparing the acquired information and the information issuing from the target model, it is able to detect image deformations resulting from unsuitable positioning of the objective of the photographic apparatus, positioned at a low angle for example. In one embodiment, information from one or more previous updated models are used to refine the acquired information.

At step c), a comparison is made between the updated model and the target model.

Preliminary processing of the target model may be necessary for this purpose. For example, when the updated model preferably has a photo, the processing module 22 has means by which it is possible to identify, in the target model, the view presenting the greatest similarity to said photo. This view is then compared to said photo.

The comparison between the target model and the updated model may be carried out using two well-known algorithms:

Algorithms for comparison between 2D representations such as photos: These algorithms compare photos that are taken from the same viewpoint and/or that are deduced by analysis of a 3D model, especially in order to determine a view of this model corresponding to the desired orientation.

Algorithms for comparison between two three-dimensional models: A three-dimensional target model is then compared to a three-dimensional updated model, for example obtained by 3D extrapolation of 2D representations. This comparison may be carried out automatically or semi-automatically using what are known as 3D best-fit algorithms or manually using 3D alignment tools, especially by selecting, on each of the models, three points corresponding to identical sites. Alternatively, it is possible to calculate the difference in distance between characteristic points on the target model and the distance between these same characteristic points on the updated model. These characteristic points are preferably the cuspid points of the patient's teeth.

Preferably, the target model is loaded onto the personal apparatus by the party that created it, which limits the risks of disclosure of personal information. The comparison may then be made by the specialized app.

The comparison traditionally supplies a "distance" between the two models.

This distance may be interpreted directly by the patient, the orthodontist or the dentist. Preferably, the comparison module 24 compares said distance with an acceptance threshold and supplies practical information. In particular, if the distance is below the acceptance threshold, the practical information may be that no action is to be taken, whereas, if the distance is above the acceptance threshold, the practical information may be to the effect that a checkup visit to the dentist or orthodontist should be made.

In one embodiment, the comparison module supplies different practical information depending on the position of said distance with respect to several thresholds. For example, when the distance exceeds a critical threshold, the practical information may consist in conveying the need to consult the dentist or orthodontist as a matter of urgency.

The one or more thresholds used by the comparison module may be predetermined. In one embodiment, they may be parameterized. Preferably, they may be fixed and modified at any time, in particular by a dental professional.

Depending on the practical information received, the patient may visit the orthodontist or dentist in order to receive therapeutic or preventative treatment.

Preferably, the implementation of a step c) immediately brings about the establishment of a new time frame for carrying out new steps b) and c). Advantageously, the monitoring of the possible deviation of the teeth is thus permanent.

In one embodiment, the practical information is used to modify the time interval after which the patient will have to be alerted that a new updated model needs to be created.

In one embodiment, the individual apparatus makes it possible to display images, or even a sequence of images showing the position of the teeth at different dates. These images may be presented in the form of an animation.

The communication module 25 is optional, particularly if, at step a), the target model and the specialized app have been loaded onto the personal apparatus.

It allows the personal apparatus 18 to receive the reminders intended for the patient, but also information that is useful for the other modules, for example information relating to the target model, especially in order to create locating marks. The communication module 25 also makes it possible, if need be, to transmit the updated model and/or the results of the comparison made at step c), and in particular practical information, especially to a dentist or to an orthodontist.

Said information may be transmitted immediately or at predetermined moments. For example, the updated models may be sent to the orthodontist, especially in the form of reports, at a parameterizable frequency.

The communication module 25 is preferably configured to transmit and/or receive data in a secure manner.

For example, the communication may be performed, at least in part, by radio, preferably using at least one protocol chosen from among the protocols edge, 3G, 4G, udmsa, hpdmsa, Bluetooth and Wi-Fi, or using any other protocol, current or future, that is suitable for mobile or nomadic equipment, by wired synchronization with the personal computer, or by optical transmission.

As is clear at present, a method according to the invention permits precise and effective monitoring of developments in the position of the patient's teeth, substantially without any stress for the patient. The patient may thus easily implement this method, and the risk of relapse is thus greatly reduced.

This method is not in any way involved in maintaining the teeth in their position at the end of treatment. It does not replace the fitting of a retainer at the end of treatment.

Of course, the invention is not limited to the embodiments that have been described above and that are illustrated.

Preferably, the processing of the acquired images and the comparison are carried out by the same personal apparatus as the one that performs the acquisition. It is also preferable that the target model is loaded onto this personal apparatus, preferably by the orthodontic practice or the orthodontic laboratory that created the target model. Advantageously, the communication of confidential data is thereby limited.

However, several different apparatuses may also be used. For example, the acquisition may be performed with a cell phone, and the processing and comparison by a fixed computer.

Furthermore, the processing of the captured images and/or the comparison are not necessarily implemented in the personal apparatus. In particular, one or more of these modules may be implemented in a dental practice, an orthodontic practice or an orthodontic laboratory. For example, in one embodiment, step b) may be implemented by the dentist or the orthodontist.

Thus, all of the features that relate to the personal apparatus and that have been described above may be applied to the apparatus used by the dentist or the orthodontist.

Acquisition by the dentist or the orthodontist advantageously permits good positioning of the patient, which ensures precise images and improves the quality of the comparison.

In addition, the safety of the transfer of information relating to the target model or to the updated model (especially if the comparison is made outside the premises of the dentist or of the orthodontist) is advantageously improved in this way.

Preferably, the acquisition module and/or the processing module and/or the comparison module are then integrated in the professional equipment of the dentist or orthodontist. It is also preferable that the acquisition is performed in predetermined positions, preferably automatically, that is to say without the intervention of the dentist or orthodontist.

For the dentist, the implementation of the method advantageously makes it possible to detect shifts that are imperceptible to the eye, for example a loss of expansion, or shifting of the teeth with respect to a target model which does not correspond to an ideal position but, for example, the best position that the orthodontic treatment has been able to produce.

Moreover, the field of application of a method according to the invention is not limited to the detection of a deviation in the position of the teeth in order, subsequently, to take measures to counteract this deviation.

A method according to the invention may also be used to monitor the development of the position of the teeth independently of an orthodontic treatment, for example to measure the speed at which the teeth move. Such a measurement may be useful for study purposes.

By repeating steps b) and c), it is also possible to evaluate the speed at which an orthodontic treatment causes the position of the teeth to change, and thereby to measure the efficacy of this treatment. In this embodiment, step a) is optional.

A method according to the invention may be used, for example, for remote monitoring of the course of an orthodontic treatment, thereby optimizing visits by patients to their orthodontists.

The target model does not necessarily correspond to an optimal position of the teeth. A method according to the invention may thus be used in the context of an orthodontic treatment. In particular, the target model may be a theoretical model that the orthodontic treatment seeks to attain. By implementing the method, the patient is thus able, when he so desires, to evaluate the change in position of his teeth and assess the approximation to the theoretical model.

Finally, the patient is not limited to a human being. In particular, a method according to the invention may be used for another animal.

The invention claimed is:

1. A method for monitoring a position of a patient's teeth in order to monitor a relapse after an orthodontic treatment modifying the position of the patient's teeth by means of an active retainer apparatus or an apparatus comprising an arch wire and brackets, the method comprising:

a) less than 6 months after an end of the orthodontic treatment, wherein the end of the orthodontic treatment is a time when the patient is no longer wearing any active apparatus or apparatus comprising an arch wire and brackets, modeling, with a three-dimensional scanner, a target position of the teeth in a form of a target model in three dimensions, said target model modeling the teeth in their corrected position resulting from the implementation of the orthodontic treatment;

b) after a time interval greater than 1 month after step a), acquiring one or more photos and/or videos of the patient's teeth with a cell phone, under direction of the patient, processing the acquired one or more photos and/or videos of the patient's teeth from the cell phone to create a digital updated model in three dimensions, and comparing the target model and the digital updated model via an algorithm for comparison between two three dimensional models; and c) determining a difference with respect to one or more positions of the patient's teeth between the target model and the digital updated model based upon the comparing, generating information relating to the difference, and transmitting the information to the patient and/or to a dental professional.

2. The method as claimed in claim 1, in which, at step a), the modeling is carried out such that the target model supplies information concerning the position of the teeth with an error of less than 1/10 mm.

3. The method as claimed in claim 1, in which the cell phone is used to implement step c).

4. The method as claimed in claim 3, in which, prior to step b), the patient or the dental professional loads the target model onto the cell phone.

5. The method as claimed in claim 1, in which the one or more photos and/or videos comprise one or more photos of the patient's teeth.

6. The method as claimed in claim 1, in which, at step b), the one or more photos and/or videos comprise one or more images from one or more videos of the patient's teeth.

7. The method as claimed in claim 1, in which, depending on the comparison at step b), informing the patient and/or the dental professional of a probable need for a consultation with a dentist or an orthodontist.

8. The method as claimed in claim 1, in which the cell phone transmits the updated model and/or results of the comparison carried out at step b) to a dentist or to an orthodontist.

9. The method as claimed in claim 1, in which the comparison of the models is carried out either on the cell phone, or with an app used by the dental professional, or with a dedicated third-party server.

10. The method as claimed in claim 1 further comprising using the information generated at step c) to
detect a relapse, and/or
determine a speed of change in the position of teeth, and/or
optimize a scheduling of visits to an orthodontist or a dentist, and/or
evaluate an efficacy of an orthodontic treatment, and/or
evaluate the change of position of teeth toward a theoretical model corresponding to a defined position of the teeth.

11. The method as claimed in claim 1, wherein a view of the target model presenting a greatest similarity to the acquired one or more photos and/or videos is used for the comparing.

12. The method as claimed in claim 1, wherein the one or more photos and/or videos of the patient's teeth are acquired while the patient positions a retractor or an intra-oral imaging device.

13. The method as claimed in claim 1, wherein, at step b), positioning of the cell phone for acquiring the one or more photos and/or videos of the patient's teeth is guided by visual messages and/or audio messages.

14. The method as claimed in claim 1, wherein the interval is determined by the patient.

15. The method as claimed in claim 1, wherein the processing of the acquired one or more photos and/or videos of the patient's teeth from the cell phone to create the digital updated model in three dimensions, and the comparing of the target model and the digital updated model via an algorithm for comparison between two three dimensional models, in step b) is carried out by the cell phone.

\* \* \* \* \*